United States Patent [19]

Knauf et al.

[11] Patent Number: 5,220,045

[45] Date of Patent: Jun. 15, 1993

[54] PROCESS FOR THE PRODUCTION OF METAL CARBOXYLATES AND THEIR USE FOR THE POLYMERIZATION OF MONOMERS SUITABLE FOR ZIEGLER-NATTA POLYMERIZATION

[75] Inventors: Thomas Knauf, CDN-Sarnia, Canada; Werner Obrecht, Moers, Fed. Rep. of Germany

[73] Assignee: Bayer Aktiengesellschaft, Leverkusen, Fed. Rep. of Germany

[21] Appl. No.: 874,384

[22] Filed: Apr. 27, 1992

[30] Foreign Application Priority Data

May 8, 1991 [DE] Fed. Rep. of Germany ....... 4115034

[51] Int. Cl.$^5$ .......................... C07F 7/00; C07F 15/04; C07F 15/06
[52] U.S. Cl. ..................................... 556/55; 556/136; 556/149
[58] Field of Search ........................... 556/55, 136, 149

[56] References Cited

U.S. PATENT DOCUMENTS

| | | | |
|---|---|---|---|
| 4,404,408 | 9/1983 | Wirth et al. | 568/680 |
| 4,438,038 | 3/1984 | Petronella | 260/414 |
| 4,824,611 | 4/1989 | Cells | 260/414 |
| 4,921,986 | 5/1990 | Fox | 556/149 |
| 5,021,596 | 6/1991 | Barfurth et al. | 556/55 |

OTHER PUBLICATIONS

CRC Handbook of Chemistry and Physics, CRC Press, 63rd Ed. pp. B-159 and B-160 (1982).

*Primary Examiner*—José G. Dees
*Assistant Examiner*—Porfirio Nazario
*Attorney, Agent, or Firm*—Connolly & Hutz

[57] ABSTRACT

Metal carboxylates which may be used for the polymerization of monomers suitable for Ziegler-Natta polymerization are prepared by reaction of the organic $C_{2-20}$ carboxylic acids on which the carboxylates are based with ammonia and/or amines and/or tetraalkyl ammonium hydroxides and the corresponding metal nitrates in the presence of inert organic solvents at temperatures of 0° to 150° C.

10 Claims, No Drawings

PROCESS FOR THE PRODUCTION OF METAL CARBOXYLATES AND THEIR USE FOR THE POLYMERIZATION OF MONOMERS SUITABLE FOR ZIEGLER-NATTA POLYMERIZATION

This invention relates to a process for the production of metal carboxylates, more particularly carboxylates of the transition metals, the lanthanides and actinides, and to the use of the metal carboxylates for the polymerization of monomers, particularly dienes, which are suitable for Ziegler-Natta polymerization.

The production of metal carboxylates of the type mentioned, particularly carboxylates of the rare earths, such as neodymium carboxylates, is known (see, for example, GB 2,140,435 and Jp 61/176 554).

For example, it is known from GB 2,140,435 that the reaction of aqueous neodymium chloride solution with three equivalents of an aqueous sodium versatate solution gives the desired neodymium versatate. The neodymium versatate thus obtained is purified by extraction with toluene and subsequent filtration of the toluene solution of the neodymium versatate.

In addition, it is known from JP 61/176Z554 that neodymium octanoate can be produced from neodymium acetate and sodium octanoate. The neodymium acetate is prepared from neodymium chloride and an excess of acetic acid. After its preparation, the neodymium octanoate is purified by recrystallization.

The disadvantage of these known processes lies, for example, in the use of NaOH as base. In excess, it leads to the partial decomposition of neodymium carboxylate. In addition, sodium remains in the product. Moreover, the above processes comprise two (GB 2,140,435) or three (JP 61/176 554) separate reaction steps which involve considerable outlay on equipment (several tanks, metering systems, etc.). Solids accumulate in both processes and have to be extracted and filtered, the solvent having to be replaced (GB 2,140,435) or the end product having to be subsequently purified by recrystallization (JP 61/176 554). This results in considerable losses of yield.

It has now been found that the above-mentioned disadvantages in the production of metal carboxylates can be avoided if the organic $C_{2-20}$ carboxylic acids on which the carboxylates are based are reacted with ammonia and/or amines and/or tetraalkyl ammonium hydroxides and the corresponding metal nitrates in the presence of inert organic solvents at temperatures of 0° to 150° C.

The process according to the invention may be represented by the following general formula:

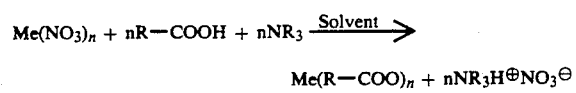

$$Me(NO_3)_n + nR-COOH + nNR_3 \xrightarrow{Solvent}$$
$$Me(R-COO)_n + nNR_3H^\oplus NO_3^\ominus$$

The metal nitrates used in the process according to the invention are, in particular, the nitrates of the lanthanides, the transition metals of the 3rd, 4th and 8th group of the periodic system (excluding titanium) and the actinides. Suitable metal nitrates are, for example, the nitrates of iron, cobalt, nickel, cerium, praseodymium, neodymium, samarium, europium, gadolinium, terbium, dysprosium, holmium, erbium, thulium, ytterbium, lutetium, thorium, scandium, ytterbium, and lanthanum, the nitrates of the nitrates of cerium, praseodymium, neodymium, cobalt and nickel being preferred. The metal nitrates may of course be used in admixture with one another. Although they may be mixed in any ratio, the mixing ratio will normally be determined by the application envisaged for the metal carboxylate.

The organic carboxylic acids used are aliphatic and cycloaliphatic carboxylic acids, preferably those containing 2 to 18 carbon atoms. Particularly preferred organic carboxylic acids correspond to the following formula

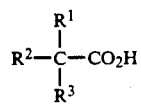

$$R^2-\underset{\underset{R^3}{|}}{\overset{\overset{R^1}{|}}{C}}-CO_2H$$

in which $R^1$, $R^2$ and $R^3$ may be the same or different and represent hydrogen or $C_{1-10}$ alkyl radicals, the sum of the carbon atoms of $R^1$, $R^2$ and $R^3$ being from 0 to 16 C atoms.

Aromatic organic carboxylic acids may also be used, those containing 7 to 19 carbon atoms being preferred. Aromatic organic carboxylic acids corresponding to the formula

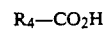

$$R_4-CO_2H$$

in which $R_4$ is an aryl radical or a $C_{6-17}$ alkylaryl radical.

The following carboxylic acids are mentioned as examples: acetic acid, propionic acid, n-butyric acid, isobutyric acid, valeric acid, pivalic acid, hexane carboxylic acid, 2-hexane carboxylic acid, cyclohexane carboxylic acid, 3-cyclohexyl propionic acid, 2-ethyl hexane carboxylic acid, 2-methyl-2-ethyl pentanoic acid, 2,2-diethyl pentanoic acid, 2,2-dimethyl hexanoic acid, 2-methyl-2-ethyl hexanoic acid, 2,2-diethyl hexanoic acid, 2-ethyl-2-propyl hexanoic acid, 2-ethyl-2-butyl heptanoic acid, 2,2-diethyl heptanoic acid, 2,2-diethyl octanoic acid and 2-methyl-2-butyl octanoic acid, 1-heptanoic acid, 1-octane carboxylic acid, 1-nonane carboxylic acid, versatic acid (a commercial product of Shell Chemie), lauric acid, myristic acid, palmitic acid, stearic acid, oleic acid, benzoic acid, naphthalene acid, phenyl acetic acid, triphenyl acetic acid, tricyclohexyl acetic acid, preferably pivalic acid, cyclohexane carboxylic acid and 2-ethyl hexane carboxylic acid.

The organic carboxylic acids mentioned may be used both individually and in admixture with one another. The most favorable mixing ratio may readily be determined by suitable preliminary tests.

The amines used in the process according to the invention correspond to the following formula

$$NR_3$$

in which the R's may be the same or different and represent methyl, ethyl, propyl, butyl or pentyl and their isomers.

The tetraalkyl ammonium hydroxides used in the process according to the invention correspond to the following formula

$$NR_4OH$$

in which the R's may be the same or different and represent methyl, ethyl, propyl, butyl, pentyl, hexyl, heptyl, octyl or benzyl and their corresponding isomers.

Both the ammonia and the amines may be used in gaseous o form, in liquid form or in aqueous solution (10 to 30%). The tetraalkyl ammonium hydroxides are preferably used in the form of an aqueous solution (20 to 80%).

The process according to the invention is preferably carried out at temperatures of 20° to 40° C. and may be carried out in the absence of pressure and also under pressure (1 to 50 bar).

The inert organic solvents used for the process according to the invention may be any of those normally used for Ziegler-Natta polymerizations. Suitable inert organic solvents are, for example, aliphatic, cycloaliphatic or aromatic hydrocarbons containing 4 to 20 carbon atoms and preferably 4 to 10 carbon atoms, such as butane, pentane, hexane, heptane, octane, cyclohexane, cyclodecane and toluene and also their corresponding isomers, preferably n-hexane and cyclohexane.

The most suitable inert organic solvents for the process according to the invention may readily be determined by corresponding preliminary tests. The inert organic solvents may be used both individually and in admixture with one another.

In the process according to the invention, approximately 2 to 6 mol and preferably 2 to 4 mol organic carboxylic acid is normally used per mol metal nitrate.

Depending on the valency of the parent metal, the molar ratio of the metal nitrate to be used to ammonia and/or amine and/or tetraalkyl ammonium hydroxide is 1:2 to 10 (divalent) or 1:3 to 15 (trivalent) or 1:4 to 20 (tetravalent).

It has proved to be of advantage to the process according to the invention to measure the quantity of inert organic solvent used in such a way that concentrations of the metal carboxylate in the solvent of about 0.1 to 80% by weight and preferably 5 to 60% by weight are obtained.

The process according to the invention may be carried out, for example, by initially introducing the corresponding quantities of inert organic solvent, metal nitrate and organic carboxylic acid and subsequently introducing the corresponding quantity of ammonia and/or amine and/or tetraalkyl ammonium hydroxide with vigorous stirring at the temperatures mentioned above. After the exothermic reaction, the aqueous phase formed is separated off and the organic phase is repeatedly extracted with water. To recover the metal carboxylates, the water is then distilled off by azeotropic distillation.

Metal carboxylates which are insoluble in the solvents mentioned above are repeatedly washed with water and dried (in a drying cabinet at approx. 80° C./16 torr).

The present invention also relates to the use of the metal carboxylates produced by the process according to the invention for the polymerization of monomers suitable for Ziegler-Natta polymerization.

The monomers in question are, in particular, dienes, such as butadiene, isoprene, 2-phenyl butadiene, 2,3-dimethyl butadiene, 1,3-hexadiene and 1,3-octadiene.

The polymerization of monomers such as these is known and is described, for example, by John Boor Jr., Ziegler-Natta Catalysts and Polymerizations, Academic Press, New York/San Francisco/London, 1979.

The metal carboxylates according to the invention, particularly the carboxylates of the rare earths, are particularly suitable for the polymerization of conjugated dienes (see, for example, EP 007 027, DE 3 224 288, EP 011 184, EP 0 201 979, EP 0 201 962, EP 0 127 236, EP 0 207 558).

The polymerization of the dienes results in the formation of valuable elastomers which in turn are suitable, for example, for the production of tires, golf balls and other rubber products.

EXAMPLES

A. 0.418 mol aqueous neodymium nitrate solution and 1.317 mol versatic acid in 1665 ml cyclohexane are introduced into a 4 liter flask. 1.267 mol ammonia is then introduced with vigorous stirring at room temperature. On completion of the reaction, the reaction mixture is extracted twice with 100 ml distilled water. Residual water is then removed from the 17.5% violet neodymium versatate solution in cyclohexane by azeotropic distillation.

B. Using a 1 liter flask, 0.40 mol triethylamine is added with stirring at room temperature to 0.40 mol 2-ethyl hexane carboxylic acid. After the exothermic reaction has abated, the reaction mixture is diluted with 65 ml cyclohexane and 0.20 mol cobalt nitrate is added. After stirring for 30 minutes, the reaction solution is filtered, leaving a 55.5% blue cobalt octoate solution in cyclohexane.

C. 0.10 mol aqueous neodymium nitrate solution, 0.30 mol versatic acid and 1606 ml cyclohexane are introduced into a 4 liter flask. 0.303 mol aqueous tetrabutyl ammonium hydroxide solution (40%) is then added with vigorous stirring at room temperature. On completion of the exothermic reaction, the organic phase is extracted 5 times with 200 ml water. Water is then removed from the neodymium versatate solution in cyclohexane by azeotropic distillation.

D. 0.303 mol aqueous ammonia solution (25%) is added with vigorous stirring at room temperature to an emulsion of 0.30 mol pivalic acid in 0.10 mol aqueous neodymium nitrate solution. An exothermic reaction occurs and a pink-colored deposit is precipitated. The deposit is removed by centrifugation and washed repeatedly with water. Drying in vacuo for 15 hours at 80° C. leaves 41.8 g neodumium pivalate.

E. 0.32 mol ammonia is added with vigorous stirring at room temperature to an emulsion of 0.10 mol aqueous neodymium nitrate solution, 0.1575 mol cyclohexane carboxylic acid and 0.1575 mol versatic acid in 1050 ml cyclohexane. After the exothermic reaction has abated, the reaction mixture is extracted twice with 100 ml water. The violet neodymium carboxylate solution is dried by azeotropic distillation.

We claim:

1. A process for the production of metal carboxylates, which are based on $C_{2-20}$ carboxylic acids, wherein the $C_{2-20}$ carboxylic acids on which the carboxylates are based are reacted with a) metal nitrates, wherein the metal constituent of the metal nitrate is selected from the group consisting of the transition metals of the 3rd, 4th and 8th groups of the periodic system (excluding titanium), the lanthanides and the actinides, and corresponds to the metal constituent of the metal carboxylate, and b) at least one of ammonia, amines and tetraalkyl ammonium hydroxides in the presence of at least one inert organic solvent at temperatures of 0° to 150° C.

2. A process as claimed in claim 1, wherein the $C_{2-20}$ carboxylic acids used correspond to the following formula $$R^2-\underset{\underset{R^3}{|}}{\overset{\overset{R^1}{|}}{C}}-CO_2H$$

in which
$R^1$, $R^2$ and $R^3$ may be the same or different and represent hydrogen or $C_{1-10}$ alkyl radicals, the sum of the carbon atoms of $R^1$, $R^2$ and $R^3$ being from 0 to 16 C atoms,
or to the following formula $$R_4-CO_2H$$

in which
$R^4$ is an aryl radical or a $C_{6-17}$ alkylaryl radical.

3. A process as claimed in claim 1, wherein the amines correspond to the following formula $$NR_3$$

in which
the R's may be the same or different and are selected from the group consisting of methyl, ethyl, propyl, butyl, pentyl and their isomers.

4. A process as claimed in claim 1, wherein the tetraalkyl ammonium hydroxides correspond to the following formula $$NR_4OH$$

in which
the R's may be the same or different and are selected from the group consisting of methyl, ethyl, propyl, butyl, pentyl, hexyl, heptyl, octyl, benzyl and their corresponding isomers.

5. A process as claimed in claim 1, wherein the at least one of ammonia, amines and tetraalkyl ammonium hydroxides are used in aqueous solution.

6. A process as claimed in claim 1, wherein the metal nitrates are selected from the nitrates of cerium, praseodymium, neodymium, cobalt and nickel.

7. A process as claimed in claim 1, wherein said at least one inert organic solvent comprises at least one hydrocarbon selected from the group consisting of aliphatic, cycloaliphatic and aromatic hydrocarbons containing 4 to 20 carbon atoms.

8. A process as claimed in claim 1, wherein 2 to 6 mol of said $C_{2-20}$ carboxylic acid are used per mol of said metal nitrate.

9. A process as claimed in claim 1, wherein 2 to 20 mol of said at least one of ammonia, amines and tetraalkyl ammonium hydroxides are used per mol of said metal nitrate.

10. A method of using the metal carboxylates produced by the process in claim 1, wherein said method comprises polymerizing monomers suitable for Ziegler-Natta polymerization in the presence of said metal carboxylate.

* * * * *

UNITED STATES PATENT AND TRADEMARK OFFICE
CERTIFICATE OF CORRECTION

PATENT NO. : 5,220,045
DATED : June 15, 1993
INVENTOR(S) : Knauf, et al

It is certified that error appears in the above-indentified patent and that said Letters Patent is hereby corrected as shown below:

Claim 10, column 6, line 33-34, "carboxylate" should be -- carboxylates --.

Signed and Sealed this

Twelfth Day of April, 1994

Attest:

BRUCE LEHMAN

Attesting Officer

Commissioner of Patents and Trademarks